US005888578A

United States Patent [19]

Sanduja et al.

[11] Patent Number: 5,888,578
[45] Date of Patent: Mar. 30, 1999

[54] DISPOSABLE TOOTHBRUSH HAVING MINT FLAVORED TOOTHPASTE COMPOSITION BONDED TO BRISTLES THEREOF

[75] Inventors: Mohan L. Sanduja, Flushing, N.Y.; Kenneth Sugathan, Piscataway, N.J.; Carl Horowitz; Lina Zilberman, both of Brooklyn, N.Y.

[73] Assignee: GMZ Holding Company, Jericho, N.Y.

[21] Appl. No.: 97,228

[22] Filed: Jun. 12, 1998

Related U.S. Application Data

[62] Division of Ser. No. 742,462, Nov. 1, 1996, Pat. No. 5,783,249, Division of Ser. No. 409,909, Mar. 23, 1995, Pat. No. 5,605,736, which is a continuation of Ser. No. 150,599, Nov. 10, 1993, abandoned, which is a continuation-in-part of Ser. No. 121,161, Sep. 14, 1993, abandoned.

[51] Int. Cl.⁶ .................. A46B 11/00; B05D 1/36
[52] U.S. Cl. .................. 427/2.29; 427/412.1; 427/419.5; 15/167.1
[58] Field of Search .................. 427/2.29, 412.1, 427/419.5; 15/167.1

[56] References Cited

U.S. PATENT DOCUMENTS

| | | | |
|---|---|---|---|
| 2,099,688 | 11/1937 | Hill et al. | 300/21 |
| 2,099,888 | 11/1937 | Hill et al. | 300/21 |
| 2,893,036 | 7/1959 | Filler et al. | 15/176 |
| 3,076,218 | 2/1963 | Cook et al. | 15/159 |
| 3,231,925 | 2/1966 | Conder | 15/605 |
| 3,302,230 | 2/1967 | Poppelman | 15/167 |
| 3,378,870 | 4/1968 | Matsunaga | 15/104.94 |
| 3,401,049 | 9/1968 | Horowitz | 117/47 |
| 3,691,585 | 9/1972 | Flom | 15/104.94 |
| 3,698,931 | 10/1972 | Horowitz | 117/47 |
| 3,771,536 | 11/1973 | Dragan | 132/89 |
| 3,879,139 | 4/1975 | Dahl et al. | 401/135 |
| 4,030,845 | 6/1977 | Deckert | 401/268 |
| 4,033,365 | 7/1977 | Klepak et al. | 132/89 |
| 4,033,852 | 7/1977 | Horowitz et al. | 208/8 |
| 4,051,090 | 9/1977 | Horowitz et al. | 260/23.7 |
| 4,134,935 | 1/1979 | Quiring et al. | 260/859 |
| 4,176,980 | 12/1979 | O'Neal et al. | 401/162 |
| 4,408,920 | 10/1983 | Walther et al. | 401/176 |
| 4,521,128 | 6/1985 | O'Neal | 401/183 |
| 4,873,289 | 10/1989 | Lindner et al. | 525/293 |
| 4,875,410 | 10/1989 | Lee et al. | 101/170 |
| 4,991,362 | 2/1991 | Heyer et al. | 51/400 |
| 5,002,582 | 3/1991 | Guire et al. | 623/66 |
| 5,025,596 | 6/1991 | Heyer et al. | 51/400 |
| 5,190,788 | 3/1993 | Liang et al. | 427/2 |
| 5,300,290 | 4/1994 | Spencer | 424/54 |
| 5,320,842 | 6/1994 | Spencer | 424/401 |
| 5,340,581 | 8/1994 | Tseng et al. | 424/401 |

FOREIGN PATENT DOCUMENTS

| | | |
|---|---|---|
| 26 48 289 | 10/1976 | Germany . |
| 3-220804 | 9/1988 | Japan . |
| 2 143 428 | 2/1985 | United Kingdom . |

*Primary Examiner*—Erma Cameron
*Attorney, Agent, or Firm*—Cohen, Pontani, Lieberman & Pavane

[57] ABSTRACT

A flavored toothpaste composition is bonded to the bristles of a disposable toothbrush by a process which involves the chemical grafting and polymerizing of selected monomers and prepolymers to the bristles via a free radical mechanism. This process locks in the flavor until the product can be utilized. When the toothpaste is brought into contact with an aqueous medium, such as saliva in the oral cavity, the toothpaste dissolves thereby releasing the desired flavor to the teeth and oral cavity.

32 Claims, No Drawings

DISPOSABLE TOOTHBRUSH HAVING MINT FLAVORED TOOTHPASTE COMPOSITION BONDED TO BRISTLES THEREOF

CROSS-REFERENCES TO RELATED APPLICATIONS

This application is a divisional of U.S. patent Ser. No. 08/742,462, filed Nov. 1, 1996; now U.S. Pat. No. 5,783,249, which is a divisional of Ser. No. 08/409,909, filed Mar. 23, 1995, now U.S. Pat. No. 5,605,736, which is a continuation of Ser. No. 08/150,599, filed Nov. 10, 1993, now abandoned, which is a continuation-in-part of Ser. No. 08/121,161, filed Sep. 14, 1993, now abandoned.

BACKGROUND OF THE INVENTION

To accommodate the busy and often harried traveler, disposable toothbrushes have been designed that can be used away from home, for example on a trip, or that can be offered for single use in establishments receiving the public, such as hotels and restaurants. These disposable toothbrushes have eliminated the need for a separate tube of toothpaste by incorporating in or on the brush a sufficient dose of a flavored toothpaste for brushing the teeth, the flavor being added to encourage oral hygiene practices. Many such crior art disposable toothbrushes are complex and/or expensive, as where a mechanism is included for distributing the toothpaste onto the bristles just prior to use. In other prior art disposable toothbrushes, the toothpaste is preapplied to the bristles, but such toothbrushes have proved unstable, in that the flavoring dissipates after a relatively short period of time, which is impractical as commercial considerations require a reasonable shelf life. As a result, prior art disposable toothbrushes have, for the most part, not proved commercially successful, primarily because no known prior art disposable toothbrush has satisfied the multiple criteria of a preapplied toothpaste thereby eliminating the need for a distribution mechanism, a reasonable shelf life, and a low manufacturing cost. Regarding manufacturing costs, it is well known that service establishments, such as hotels, will not provide to their patrons disposable items which exceed a preestablished cost.

Hospitals, of course, also provide toothbrushes to their patients. Typically, hospitals provide a toothbrush and a separate tube of toothpaste, the tube typically including sufficient toothpaste for a limited number of uses. This, however, poses two problems. First, there is a risk of transmission of infectious disease, as when a patient places his/her toothbrush on a sink, etc. Secondly, in the case of a patient having use of only one arm, as is sometimes the case when patients are treated intravenously, it is difficult for the patient to manipulate the toothpaste onto the bristles of the toothbrush.

For the foregoing reasons, there is a need for an individually wrapped, inexpensive disposable toothbrush having a toothpaste composition distributed over the bristles of the toothbrush and in which the flavoring does not dissipate over a reasonable shelf life.

OBJECTS AND SUMMARY OF THE INVENTION

It is therefore an object of the present invention to provide a flavored toothpaste composition bonded to a toothbrush, wherein the flavor is stabilized and long-lasting.

It is a further object of the invention to provide a disposable toothbrush which is coated with an amount of toothpaste sufficient for a single tooth brushing operation such that the toothbrush may be disposed of after initial use.

It is another object of the invention to provide a method of manufacture of a disposable toothbrush and toothpaste product with a long-lasting, stabilized flavor.

It is still another object of the invention to provide a disposable toothbrush and toothpaste product that can be produced at low cost.

It is yet another object of the invention to provide a disposable toothbrush that is both safe and convenient to use, e.g., in a hospital setting.

The present invention is thus directed to a disposable toothbrush and toothpaste product obtained by a process which involves the chemical grafting and polymerization of selected monomers and prepolymers to the bristles of the toothbrush. More particularly, the process of the present invention comprises the steps of contacting the bristles of the toothbrush (in general hereinafter being referred to as "the substrate") with a composition containing a ferrous salt as the graft initiator, a monomer/prepolymer, and a catalyst which activates polymerization by the ferrous ion, whereby the ferrous ions are reduced by the substrate with free radicals being formed as a result on the substrate. The monomer/prepolymer attaches itself to these free radical sites, thus forming an intimate covalent bond with the substrate. The toothbrush containing the toothpaste composition is then dried to complete the graft bonding of the toothpaste to the substrate.

The strength of the resulting bond can be adjusted so that the flavored toothpaste is immediately activated when brought into contact with normal mouth fluids, i.e., water and saliva, and is released by the scrubbing action of the bristles against the teeth, imparting a desirable flavor to the teeth and mouth of the user thereof.

DETAILED DESCRIPTION OF THE PRESENTLY PREFERRED EMBODIMENTS

Mechanism of Chemical Grafting

A. As Applied to Natural and Polymeric Substrates

Chemical grafting involves activation of a substrate. Once the substrate has been activated, chains of monomers linked by carbon-carbon bonds grow on the substrate, bonding to the substrate without damaging any of the existing positive characteristics of the materials involved. Many materials, both naturally occurring and synthetic, possess active hydrogens which are more reactive than the "bulk hydrogens," the tertiary hydrogen in polypropylene for example.

Thus, graft initiators (G.I.) have the capacity of removing these active hydrogens and concomitantly initiating the growth of polymer chains at the site from where the active hydrogen was removed. In the case of polypropylene, this can be represented as follows:

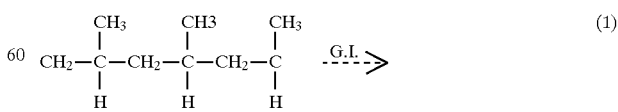

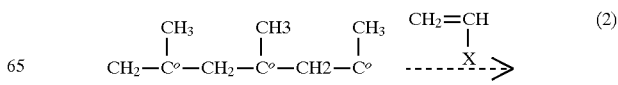

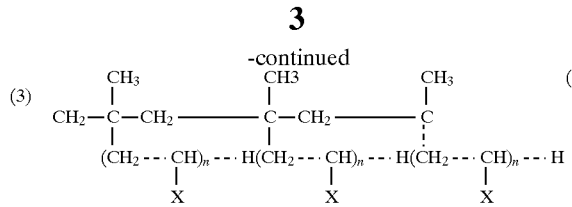

(3)

In this illustration, (°) can represent either a free radical, anion or cation, depending on whether the G.I. removes a hydrogen and one electron, no electrons or two electrons, respectively. $CH_2=CHx$ represents a unit of vinyl monomer where "x" governs the property or properties obtained. In many instances a mixture of monomers is employed and often more than one property can be altered in one processing step. These polymer chains, whose length can be controlled, are strongly attached to the substrate. The linkage between the graft polymer and the substrate is covalent in nature, and therefore, the graft polymer cannot be leached from the substrate. In essence, chemical grafting is a matter of growing polymer chains on the backbone chain of a substrate. The graft polymer chains are formed from vinyl monomers or monomers containing appropriate functionality, e.g., groups such as hydroxyl, carboxyl, epoxy, amide, amine, anhydride.

B. Chemical Grafting as Applied to a Nylon, Polypropylene or Polyester Substrate of a Toothbrush In the case of a nylon, polypropylene or polyester substrate, such as a toothbrush bristle, the chemical grafting is carried out via the abstraction of the hydrogen atom from the —CONH— group (nylon),

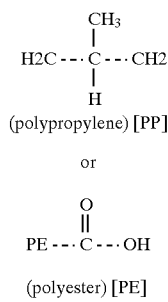

(polypropylene) [PP]

or $$PE\text{---}\overset{\overset{\displaystyle O}{\|}}{C}\text{---}OH$$

(polyester) [PE]

with the graft initiator to form a free radical which then reacts with a monomer/prepolymer solution, by which graft polymerization commences. The sequence of reaction steps involved in the chemical attachment of the monomer/prepolymer onto the toothbrush substrate is believed to take place as follows:

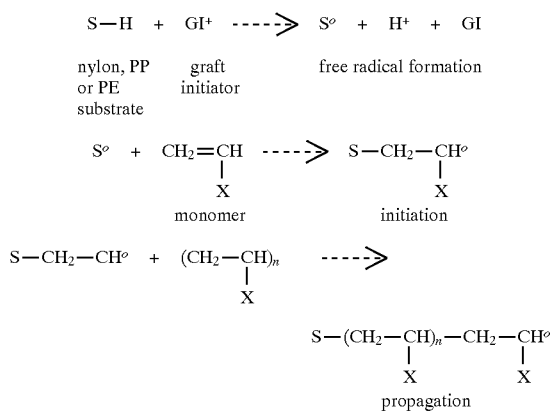

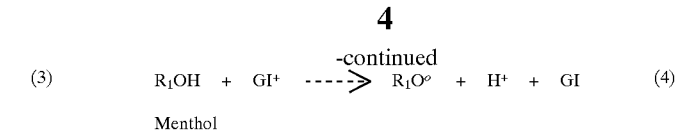

The graft polymerization shown in steps (1)–(4) may be terminated by radical combination which may occur as:

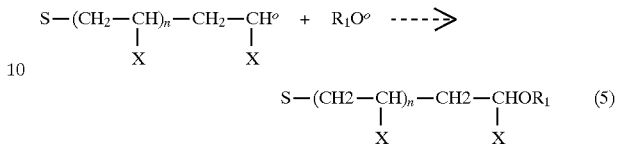

The foregoing reactions take place in the presence of a peroxide which concurrently regenerates the graft initiator forming a free radical as shown in reaction step (4).

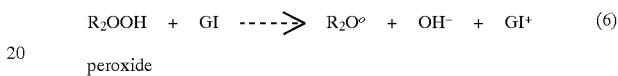

Reaction (1) provides a radical site on an exemplary substrate (S-H) by the reduction of the graft initiator and oxidation of the substrate to transform the substrate into a free radical. Reaction (2) illustrates the grafting of an exemplary monomer to the activated substrate (S°) at the free radical site to form a graft polymer radical on the substrate. This is followed by propagation in reaction (3). Reaction (4) illustrates the formation of a menthol radical, e.g.; from a peppermint compound. Reaction (5) illustrates chain termination via combination of the menthol radical with the activated substrate graft polymer formed in step (3), the end result being the chemical attachment of a monomer mint prepolymer to the surface of the toothbrush bristles. Reaction (6) illustrates the regeneration of the graft initiator ion by the presence of peroxide in the monomer solution.

Method of Preparation of the Mint-Flavored Toothpaste Formulation

The present invention is directed to a polymeric toothpaste composition that is chemically grafted to the bristles of a toothbrush to form a strong adhesion to the bristles over an extended period of time. As previously stated, chemical grafting involves the use of monomers/prepolymers, a catalyst, and a graft initiator along with other excipients in the composition.

The monomers and prepolymers are vinyl monomers and acrylic and vinyl prepolymers which chemically bond to the bristles via a Free radical system. The monomers and prepolymers are preferably acrylic monomers having one or more hydroxyl and carboxyl groups. Some of the monomers and prepolymers of this type are the following: polyvinyl alcohol, acrylic acid, polyacrylic acid, methacrylic acid, ethyl acrylate, ethyl methacrylate, isobutylmethacrylate, and methyl acrylate. Also, mixtures of two or more monomers can be used. Polyvinyl alcohol, acrylic acid and polyacrylic acid are preferred.

The formulation is prepared by taking the ingredients in the order as indicated in the examples or any other convenient order.

Ferrous ions are preferred as graft initiators for the grafting of desired monomers/prepolymers onto the bristles, but other metal ions such as Ag ions could also be used or any other metal ion which is safe for mouth application.

The presence of a small amount of a peroxide catalyst, preferably hydrogen peroxide, helps to regenerate the graft initiator system in the process which in turn provides free radicals for further chain graft polymerization. Other representative peroxides include peracetic acid and urea peroxide.

The amounts of the reactants employed is not a critical feature of the invention. For obvious economical reasons, the amounts of monomer/prepolymer, graft initiator and catalyst employed in the system will be the minimum amounts necessary to complete the reaction as previously described herein. The amounts of monomer and prepolymer employed will normally range from about 0.0001% to about 2% by weight of the composition, though the preferred concentration ranges from about 0.0001% to about 0.2% by weight. The amount of graft initiator ranges from about 0.00001% to about 0.01% by weight, preferably from about 0.00001% to about 0.001%. The amount of peroxide catalyst employed will normally range from about 0.001% to about 1% by weight, preferably from about 0.001% to about 0.5%.

Suitable materials for use as flavors are those which allow the user to detect a strong, noticeable flavor while permitting maintenance of an acceptable product appearance. The flavors may be of natural or synthetic origin. Such flavors include peppermint, spearmint, wintergreen, cinnamon, and the like; fruit flavors such as cherry, strawberry, lime, and the like. Preferred flavors for use in toothpaste include peppermint and spearmint.

Examples of auxiliary excipients utilized in the present invention include fillers, surfactants, buffers and pigments.

The formulation described herein has several advantages. First, it eliminates the need for a complex and expensive article that is intended to be used only once. Second, it eliminates, when traveling, the need for packing both a toothbrush and a tube of toothpaste. And finally, the intimate bond that is formed when the toothpaste is applied to the bristles locks in the freshness and flavor for a long period of time.

In the preferred embodiment of the invention, the bristles of the toothbrush are dipped into a toothpaste that contains monomers, prepolymers, graft initiator ions, peroxide ions and other excipients of the composition. The coated samples are then air dried at room temperature for approximately 30 to 40 minutes, whereby the hydroxyl and carboxyl groups from the monomers/prepolymers in the toothpaste polymerize to form a strong adhesion to the bristles of the toothbrush.

Where the toothpaste is applied to the bristles as a single coat, the formulation consists basically of the monomer/prepolymer, catalyst, graft initiator, pigment, flavoring and other auxiliary excipients. The desired amounts of each filler, namely calcium carbonate, sodium hydrogen carbonate, sodium lauryl sulfate, potassium tripolyphosphate and sodium fluoride are combined in a container and mixed until a homogeneous mixture is obtained. Likewise the desired amounts of the monomer/prepolymer, graft initiator and pigment are combined in a container and stirred until the solution is uniform. The mixture of fillers is then added in small increments with continuous stirring to the uniform solution. The polyacrylic acid is then added, followed by the mint flavored compound, and the contents are blended to a smooth paste. The hydrogen peroxide is finally added and the paste is mixed again until uniform. The prepared reactive formulation may then be applied to the toothbrush by dipping the toothbrush into the toothpaste and then, if necessary, the product may be exposed to air drying for 30 to 40 minutes to complete the graft bonding. If desired, the drying process may be accelerated by subjecting the product to heat, e.g., at a temperature of about 212° F. to 300° F. for 1 to 2 minutes.

The following examples illustrate formulations which may be used in the invention.

EXAMPLE 1

| Composition | Parts by Weight |
| --- | --- |
| 1. Calcium carbonate | 500.00 |
| 2. Sodium hydrogen carbonate | 20.00 |
| 3. Sodium lauryl sulfate | 15.00 |
| 4. Potassium tripolyphosphate | 2.50 |
| 5. Sodium fluoride | 1.00 |
| 6. Glycerol (solvent) | 250.00 |
| 7. Acrylic acid, 0.1% in glycerol (monomer) | 0.10 |
| 8. Graphtol green 5884-2 (pigment) | 0.10 |
| 9. Ferrous ammonium sulfate, 0.1% solution (Items 6, 7, 8 and 9 are blended together as a premix.) | 0.01 |
| 10. Polyacrylic acid, 1% solution (prepolymer) | 0.10 |
| 11. Peppermint oil | 20.00 |
| 12. Hydrogen peroxide, 0.1% solution | 0.01 |

Ingredients 1–5 (all solids) were blended together until a uniform mix was obtained. This mixture was then poured with continuous stirring to the glycerol premix of ingredients 6–9 and the resulting blend mixed again to a uniform paste. The polyacrylic acid was then added, followed by the peppermint oil, and the paste blended until smooth. Hydrogen peroxide was added and the paste was mixed again, the resulting paste being ready for use.

The bristle part of the toothbrush was dipped directly into the toothpaste and lifted up. The amount of paste on the brush was adjusted by controlling the depth the bristles sink into the paste. The paste was then air dried.

EXAMPLE 2

| Composition | Parts by Weight |
| --- | --- |
| 1. Calcium carbonate | 500.00 |
| 2. Sodium hydrogen carbonate | 20.00 |
| 3. Sodium lauryl sulfate | 15.00 |
| 4. Potassium tripolyphosphate | 2.50 |
| 5. Sodium fluoride | 1.00 |
| 6. Glycerol | 250.00 |
| 7. Acrylic acid, 0.1% in glycerol | 0.10 |
| 8. Graphtol green 585H-2 | 0.10 |
| 9. Ferrous ammonium sulfate, 0.1% solution (Items 6, 7, 8 and 9 are blended together as a premix.) | 0.01 |
| 10. Polyacrylic acid, 1% solution | 0.10 |
| 11. Spearmint oil | 20.00 |
| 12. Hydrogen peroxide, 0.1% solution | 0.01 |

The formulation in example 2 was made exactly the same as in Example 1, the only difference being that spearmint oil was substituted for the peppermint oil. The paste was applied to the brush also by the same method.

EXAMPLE 3

| Composition | Parts by Weight |
| --- | --- |
| 1. Calcium carbonate | 500.00 |
| 2. Sodium hydrogen carbonate | 20.00 |
| 3. Sodium lauryl sulfate | 15.00 |
| 4. Potassium tripolyphosphate | 2.50 |
| 5. Sodium fluoride | 1.00 |
| 6. Glycerol | 250.00 |
| 7. Acrylic acid, 0.1% in glycerol | 0.10 |

-continued

| Composition | Parts by Weight |
|---|---|
| 8. Graphtol green 5884-2 | 0.10 |
| 9. Ferrous ammonium sulfate, 0.1% solution | 0.01 |
| (Items 6, 7, 8 and 9 are blended together as a premix.) | |
| 10. Polyacrylic acid, 1% solution | 0.10 |
| 11. Peppermint oil | 20.00 |
| 12. Hydrogen peroxide, 0.1% solution | 0.01 |
| 13. Deionized water | 80.90 |

Example 3 was made exactly as Example 1 but after the first 12 ingredients were blended, water was slowly added with continuous mixing, the resulting mix blended to a smooth consistency. The bristles were dipped into the formulation and allowed to dry.

EXAMPLE 4

| Composition | Parts by Weight |
|---|---|
| 1. Calcium carbonate | 500.00 |
| 2. Sodium hydrogen carbonate | 20.00 |
| 3. Sodium lauryl sulfate | 15.00 |
| 4. Potassium tripolyphosphate | 2.50 |
| 5. Sodium fluoride | 1.00 |
| 6. Glycerol | 250.00 |
| 7. Acrylic acid, 0.1% in glycerol | 0.10 |
| 8. Graphtol green 5854-2 | 0.10 |
| 9. Ferrous ammonium sulfate, 0.1% solution | 0.01 |
| (Items 6, 7, 8 and 9 are blended together as a premix.) | |
| 10. Polyacrylic acid, 1% solution | 0.10 |
| 11. Spearmint oil | 20.00 |
| 12. Hydrogen peroxide, 0.1% solution | 0.01 |
| 13. Deionized water | 80.90 |

Example 4 was made the same way as Example 3 except for the substitution of spearmint oil for peppermint oil. The bristles were dipped into the paste and were ready for packing when dry.

Where the toothpaste is applied to the bristles in two coats, the prime coat consists basically of the flavoring and the prepolymer, whereas the top coat consists of the monomer, catalyst, graft initiator, pigment and other auxiliary excipients. The desired amount of flavor is mixed with the prepolymer and applied to the bristles by dipping, then curing at 200° F. for 4–5 minutes. The desired amounts of each filler, namely calcium carbonate, sodium hydrogen carbonate, sodium lauryl sulfate and potassium tripolyphosphate are combined in a container and mixed until a uniform mix is obtained. A solution of the pigment is prepared, added to the uniform mix, and mixed until a uniform blend is obtained. The desired amounts of the monomer, graft initiator and catalyst are then added to the blend and the contents are mixed well. The prepared formulation may then be applied as a top coat over the prime coat by dipping the already flavor-treated toothbrush into the top coat and curing at 300° F. for 2 minutes.

The following example illustrates a formulation which may be used in the invention.

EXAMPLE 5

| Composition | Parts by Weight |
|---|---|
| Prime Application | |
| 1. Polyvinyl alcohol 523 | 200.00 |
| 8% solution in water | |
| 2. Peppermint (polarome) | 30.00 |
| Top Application | |
| 3. Calcium carbonate | 1000.00 |
| 4. Sodium hydrogen carbonate | 50.00 |
| 5. Sodium lauryl sulfate | 34.00 |
| 6. Potassium tripolyphosphate | 5.00 |
| 7. Deionized water | 162.00 |
| 8. Mx 439 PYLA-Cert Green | 0.20 |
| 9. Glycerol | 500.00 |
| 10. Acrylic acid, 0.1% in glycerol | 0.20 |
| 11. Ferrous ammonium sulfate, 0.1% solution | 0.02 |
| 12. Hydrogen peroxide, 0.1% solution | 0.02 |

Ingredient 1 was prepared by adding small increments of polyvinyl alcohol to deionized water with continuous stirring until all particles were wetted out. The solution was heated to 185° F.–205° F. (85° C.–96° C.) for 30 minutes and then allowed to cool to room temperature. The peppermint was then added to this solution, mixed and applied as a prime coat to the bristles by dipping. The product was then cured at 200° F. for 4–5 minutes. Next, ingredients 3, 4, 5 and 6 were blended together until a uniform mix was obtained (Part A). Ingredients 7 and 8 were mixed well, ingredient 9 was added, and the contents mixed again (Part B). Part B was then mixed into Part A until a uniform blend was obtained (Part C). Ingredients 10, 11 and 12 were then added to Part C and mixed well for 1–2 minutes. The formulation thus prepared was ready to use as a top coat over the prime coat containing the flavor. This top coat was applied to the already treated bristles by dipping. The product was then cured at 300° F. for 2 minutes.

It should be understood that the preferred embodiments and examples described are for illustrative purposes only and are not to be construed as limiting the scope of the present invention which is properly delineated only in the appended claims.

What is claimed is:

1. A method of bonding a flavored toothpaste composition to a substrate, comprising the steps of:
   (a) providing a toothbrush having bristles comprising said substrate;
   (b) activating the substrate with a graft initiator;
   (c) bonding a monomer/prepolymer to the activated substrate;
   (d) polymerizing the monomer/prepolymer to form a graft polymer chain;
   (e) chemically bonding a flavoring to the polymer chain, steps (b) through (e) being performed in the presence of a catalyst; and
   (f) drying the toothbrush containing the flavored toothpaste composition to complete the graft polymerization whereby the flavoring is preserved until the toothbrush and flavored toothpaste composition is utilized.

2. The method of claim 1, wherein said step (a) comprises providing a toothbrush having bristles containing in their molecular structure active hydrogens for graft polymerization at vacated hydrogen sites.

3. The method of claim 1, wherein said step (a) comprises providing a toothbrush having nylon, polypropylene or polyester bristles.

4. The method of claim 1, wherein said step (b) comprises activating the substrate with a graft initiator in the form of metal ions for abstracting active hydrogens and transforming the abstracted sites into free radical sites to which the monomer/prepolymer attaches, the result being a covalent bond of the monomer/prepolymer to the toothbrush bristles.

5. The method of claim 4 wherein said step (b) comprises activating the substrate with a graft initiator in the form of ferrous ions.

6. The method of claim 1, wherein step (b) further comprises reduction of the graft initiator and oxidation of the substrate so as to form a free radical in the substrate.

7. The method of claim 1, wherein step (c) further comprises grafting the monomer/prepolymer to the activated substrate to form a graft polymer radical on the substrate.

8. The method of claim 1, wherein step (d) further comprises growing polymer chains on the substrate.

9. The method of claim 1, wherein step (e) further comprises the steps of:
  (i) forming a menthol radical; and
  (ii) combining the menthol radical with the activated substrate graft/polymer formed in step (d), the result being a covalent bonding of the flavoring to the surface of the toothbrush bristles.

10. The method of claim 1, further comprising the step of curing the toothbrush containing the flavored toothpaste composition at a temperature of about 212° F. to about 300° F. for about 1 to 2 minutes.

11. The method of claim 1, wherein said step (e) comprises chemically bonding a flavoring to the polymer chain in the presence of a peroxide catalyst.

12. The method of claim 11, wherein said step (e) comprises chemically bonding a flavoring to the polymer chain in the presence of hydrogen peroxide.

13. The method of claim 1, wherein said step (c) comprises bonding acrylic acid and polyacrylic acid to the activated substrate.

14. A method of bonding a flavored toothpaste composition to a substrate, the substrate being the bristles of a toothbrush, comprising the steps of:
  (a) applying a single coat of the toothpaste composition to the bristles of the toothbrush, the single coat including a monomer/prepolymer, a catalyst, a graft initiator, flavoring and other auxiliary excipients; and
  (b) air drying the toothbrush containing the flavored toothpaste composition.

15. The method of claim 14, wherein the single coat further comprises a pigment.

16. The method of claim 14, wherein said step (a) comprises:
  (i) activating the substrate with the graft initiator;
  (ii) bonding the monomer/prepolymer to the activated substrate;
  (iii) polymerizing the monomer/prepolymer to form a graft polymer chain; and
  (iv) chemically bonding the flavoring to the polymer chain, (i) through (iv) being performed in the presence of the catalyst.

17. The method of claim 14, wherein said step (a) comprises applying a single coat including a graft initiator in the form of metal ions for abstracting active hydrogens and transforming the abstracted sites into free radical sites to which the monomer/prepolymer attaches, the result being a covalent bond of the monomer/prepolymer to the toothbrush bristles.

18. The method of claim 17, wherein said step (a) comprises applying a single coat including a graft initiator in the form of ferrous ions.

19. The method of claim 17, wherein the single coat also includes a pigment.

20. The method of claim 18, wherein the single coat also includes a pigment.

21. The method of claim 15, wherein (i) further comprises reduction of the graft initiator and oxidation of the bristles to transform the bristles into a free radical.

22. The method of claim 16, wherein (ii) further comprises grafting the prepolymer to the activated substrate to form a graft prepolymer radical on the substrate.

23. The method of claim 16, wherein (iii) further comprises growing polymer chains on the substrate.

24. The method of claim 16, wherein (iv) further comprises:
  (a) forming a menthol radical; and
  (b) combining the menthol radical with the activated graft prepolymer substrate formed in (ii), the result being a covalent bonding of the flavoring to the surface of the toothbrush bristles.

25. The method of claim 14, wherein step (b) is conducted at room temperature for about 30 to 40 minutes.

26. The method of claim 14, further comprising the optional step (c) of curing the toothbrush containing the flavored toothpaste composition.

27. The method of claim 26, wherein step (c) is conducted at a temperature of about 212° F. to 300° F. for about one to two minutes.

28. The method of claim 14, wherein said step (a) comprises applying a single coat including a peroxide catalyst.

29. The method of claim 28 wherein said step (a) comprises applying a single coat including a hydrogen peroxide catalyst.

30. The method of claim 16, wherein (i) through (iv) are performed in the presence of a peroxide catalyst.

31. The method of claim 30, wherein (i) through (iv) are performed in the presence of a hydrogen peroxide catalyst.

32. The method of claim 14, wherein said step (a) comprises applying a single coat including an acrylic acid monomer and a polyacrylic acid prepolymer.

* * * * *